United States Patent
Young

(10) Patent No.: US 10,123,718 B2
(45) Date of Patent: Nov. 13, 2018

(54) METHODS, SYSTEMS, AND ASSEMBLIES FOR MEASURING BIOELECTRICAL SIGNALS OF INTRA-ABDOMINAL ORGANS

(71) Applicant: University of Tennessee Research Foundation, Knoxville, TN (US)

(72) Inventor: Roger Charles Young, Memphis, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 270 days.

(21) Appl. No.: 14/922,955

(22) Filed: Oct. 26, 2015

(65) Prior Publication Data

US 2016/0120435 A1 May 5, 2016

Related U.S. Application Data

(60) Provisional application No. 62/072,800, filed on Oct. 30, 2014.

(51) Int. Cl.
| | | |
|---|---|---|
| A61B 5/0492 | (2006.01) | |
| A61B 5/00 | (2006.01) | |
| A61B 5/024 | (2006.01) | |
| A61B 5/0488 | (2006.01) | |

(52) U.S. Cl.
CPC ........ *A61B 5/0492* (2013.01); *A61B 5/02411* (2013.01); *A61B 5/04882* (2013.01); *A61B 5/04884* (2013.01); *A61B 5/4356* (2013.01); *A61B 5/6832* (2013.01); *A61B 2503/02* (2013.01); *A61B 2562/04* (2013.01)

(58) Field of Classification Search
CPC .... A61B 5/0478; A61B 5/0492; A61B 5/6823
See application file for complete search history.

(56) References Cited

U.S. PATENT DOCUMENTS

| | | | | |
|---|---|---|---|---|
| 4,308,873 A | * | 1/1982 | Maynard | A61B 5/04004 600/378 |
| 4,657,023 A | | 4/1987 | Kuhn | |
| 5,237,995 A | * | 8/1993 | Cano | A61B 5/04087 600/396 |
| 5,511,553 A | * | 4/1996 | Segalowitz | A61B 5/0006 128/903 |
| 5,833,622 A | * | 11/1998 | Meathrel | A61B 5/04087 600/376 |

(Continued)

OTHER PUBLICATIONS

International Preliminary Report on Patentability on PCT/US/2015/057352.

(Continued)

*Primary Examiner* — Lee S Cohen
(74) *Attorney, Agent, or Firm* — Foley & Lardner LLP

(57) ABSTRACT

The present disclosure discuses systems and methods for detecting and recording bioelectric signals, and specifically bioelectrical signals generated by abdominal organs, such as the uterus. The disclosure discusses area electrodes and arrays of area electrodes. The area electrodes are defined in a metal layer and include an inner and outer diameter. The area electrodes are configured to detect electrical signals generated substantially perpendicular to a surface of the area electrode while rejecting electrical signals generated substantially parallel to the surface of the area electrode.

18 Claims, 12 Drawing Sheets

(56) References Cited

U.S. PATENT DOCUMENTS

| | | | |
|---|---|---|---|
| 6,073,039 A * | 6/2000 | Berson | A61B 5/04085 600/372 |
| 6,270,458 B1 * | 8/2001 | Barnea | A61B 5/1076 600/438 |
| 6,879,858 B1 * | 4/2005 | Adams | A61B 5/04882 607/39 |
| 7,925,323 B2 * | 4/2011 | Meyer | A61B 5/04085 600/382 |
| 8,615,283 B2 * | 12/2013 | Besio | A61B 5/04004 600/383 |
| 9,445,740 B1 * | 9/2016 | Crone | A61B 5/6802 |
| 2004/0199237 A1 * | 10/2004 | Mills | A61N 1/046 607/152 |
| 2007/0191728 A1 | 8/2007 | Shennib | |
| 2012/0150010 A1 | 6/2012 | Hayes-Gill et al. | |

OTHER PUBLICATIONS

Gema Prats-Boluda et al "Active concentric ring electrode for non-invasive detection of intestinal myoelectric signal." Med Eng Phys. May 2011;33(4):446-55. doi: 10.1016/j.medengphy.2010.11. 009. [retrieved on Nov. 22, 2010] abstract figures 1,3-4 Paragraph bridging pp. 446-447 p. 447 left-hand column paragraph 3 Section 2.1 and 2.2 on pp. 447 and 448 the whole document.

International Search Report & Written Opinion on PCT/US2015/057352 dated Jan. 29, 2016.

Ye-Un et al. Feasibility and analysis of bipolar concentric recording of electrohysterogram with flexible active electrode. Ann Biomed Eng. Apr. 2015;43(4):968-76. doi: 10.1007/s10439-014-1130-5. [retrieved on Oct. 2, 2014] abstract figure p. 968 last paragraph p. 969 left-hand column last paragraph Section Concentric Ring Electrode on pp. 969-970 the whole document.

\* cited by examiner

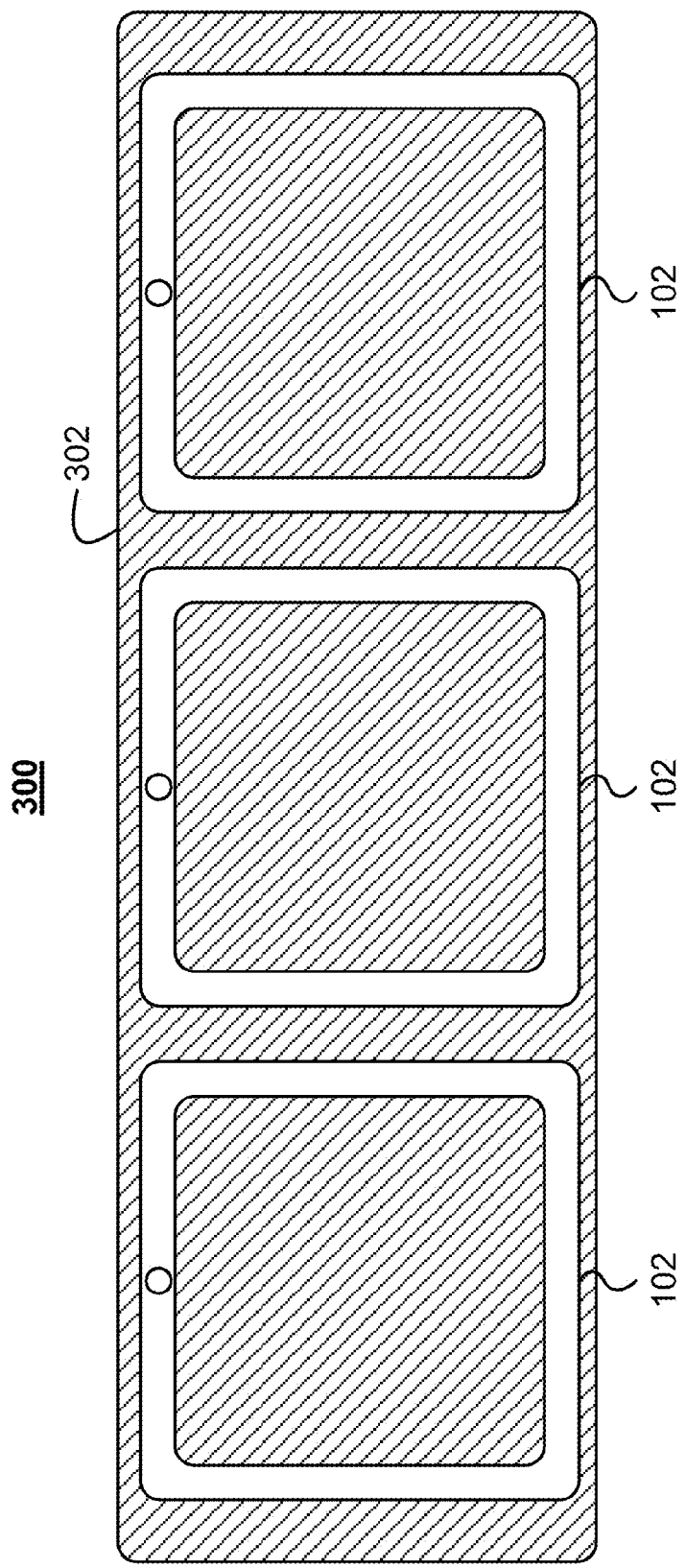

METHODS, SYSTEMS, AND ASSEMBLIES FOR MEASURING BIOELECTRICAL SIGNALS OF INTRA-ABDOMINAL ORGANS

CROSS-REFERENCE TO RELATED APPLICATIONS

This application claims priority to U.S. Provisional Patent Application No. 62/072,800 filed on Oct. 30, 2014 and titled "METHODS, SYSTEMS AND ASSEMBLIES FOR MEASURING BIOELECTRICAL SIGNALS OF INTRA-ABDOMINAL ORGANS," which is herein incorporated by reference in its entirety.

BACKGROUND

Electromyography (EMG) is the measurement of bioelectrical signals of cardiac, skeletal, or smooth muscle. Bipolar EMG technology requires measurement and amplification of the electrical potential between two contact pads. When used to detect the synchronization of regional contractions (regionality) in the uterus this technique is called uterine electromyography (uEMG). However, determining the regionality of the contractions (i.e., spatial resolution) is rendered difficult using standard bipolar EMG technology because the different regions are undefined. Further, in patients considered clinically obese, preforming EMG recordings with high signal quality is rendered even more difficult due to excess fat impeding access to the uterus.

SUMMARY

According to one aspect of the disclosure, a method for measuring at least one bioelectrical includes providing a first area electrode. The first area electrode can include a metal layer that defines an electrode body having an inner diameter and an outer diameter. The first area electrode can also include a connector in electrical communication with the metal layer. The method can include coupling the first electrode to the abdomen of a patient, and then detecting a first bioelectrical signal with the first area electrode. The first bioelectrical signal is generated from a muscle-containing intra-abdominal organ in a patient.

In some implementations of the method, the muscle-containing intra-abdominal organ is a uterus. The method can include detecting an electrical signal generated by a fetal heart or a maternal heart. The method can also include detecting, with a second area electrode, a second bioelectrical signal generated from the muscle-containing intra-abdominal organ in the patient. The first bioelectrical signal is generated by a first contractile unit of the intra-abdominal organ and the second bioelectrical signal is generated by a second contractile unit of the intra-abdominal organ. The method can include detecting a synchronization pattern of the first and the second bioelectrical signals, and determining a labor status responsive to the synchronization pattern.

In some implementations, the electrode body has one of a circular shape, a square with rounded corners shape, a hexagonal shape, a spiral shape, or a rectangle with rounded corners shape. The first area electrode can be configured to detect electrical signals originating substantially perpendicular to a surface of the electrode body, and to substantially reject electrical signals originating substantially lateral to the surface of the electrode body and environmental electrical noise. In some implementations, the electrode body has a surface area between about 5 cm$^2$ and about 900 cm$^2$.

The method can also include coupling a second area electrode to the abdomen of the patient within an opening of the first area electrode defined by the inner diameter. The method can also include determining a direction of an origination of the first bioelectrical signal.

According to another aspect of the disclosure an electrode system can include a first area electrode. The first area electrode can include a planar metal layer that defines an electrode body. The electrode body can have an inner diameter and an outer diameter. The first area electrode can also include a connector in electrical communication with the metal layer.

In some implementations, the electrode body has one of a circular shape, a square with rounded corners shape, a hexagonal shape, a spiral shape, or a rectangle with rounded corners shape. The first area electrode can be configured to detect electrical signals originating substantially perpendicular to a surface of the electrode body, and to substantially reject electrical signals originating substantially lateral to the surface of the electrode body and environmental electrical noise. The electrode body can have a surface area between about 5 cm$^2$ and about 900 cm$^2$.

In some implementations, the system also includes a second area electrode, a third area electrode, and an adhesive layer. The first area electrode can be coupled to a first portion of the adhesive layer, the second area electrode can be coupled to a second portion of the adhesive layer, and the third area electrode can be coupled to a third portion of the adhesive layer. In some implementations, the first, second, and third area electrodes are configured in a row. In other implementations, the first, second, and third area electrodes are configured in a triangle.

In some implementations, the system includes a second area electrode. The second area electrode can be positioned within an opening in the first area electrode. The opening can be defined by the inner diameter of the first area electrode. The metal layer can include silver-chloride, and the electrode body can have a width between about 0.5 cm and about 5 cm.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale; emphasis instead being placed upon illustrating the principles of the teachings. The drawings are not intended to limit the scope of the present teachings in any way. The system and method may be better understood from the following illustrative description with reference to the following drawings in which:

FIG. 3 illustrates an example electrode array for use in the system illustrate in FIG. 1A.

DETAILED DESCRIPTION

The presently disclosed patient matter will now be described more fully. The presently disclosed patient matter can, however, be embodied in different forms and should not be construed as limited to the embodiments set forth herein below and in the accompanying Examples. Rather, these embodiments are provided so that this disclosure will be thorough and complete, and will fully convey the scope of the embodiments to those skilled in the art.

The present disclosure describes systems and method for detecting and recording intra-abdominal function, contractions, fetal cardiac activity, and maternal cardiac activity. Particularly, organ-level uterine function and the contractions resulting from labor are explored, as well as the enhanced ability to measure the uterine contractions resulting from labor in patients considered clinically obese. However, the present patient matter is also applicable to other intra-abdominal "smooth muscle" contractions, e.g., contractions in the bowel, abdominal muscles, uterine contractions with and without maternal ambulation, and contractions of the non-pregnant uterus.

When determining if a patient is in true labor, not only does the contraction frequency and the strength of the contractions of the uterus need to be measured and recorded, but substantially each of the regions of the uterus should contract in synchronicity. The regions are defined by the different contractile units of the uterus. In order to determine if the regions of the uterus are contracting in synchronicity, it must be determined what regions of the uterus are contracting. The present disclosure discusses an area electrode with increased spatial resolution —providing the ability to detect the region of origination of the bioelectrical signals generated by the uterus. True labor can then be determined when a predetermined number of the regions begin to synchronously (as a function of timing, strength, and/or frequency) contract.

Past methods to attempt to determine whether the uterus is contracting involved the use of standard pad electrodes and amplifiers, such as those used in electrocardiography (EKG) in order to measure the bioelectrical signals of an organ (in this case the heart) near or beneath the EKG pads. However, when EKG pads are placed on the abdomen of a patient in order to record contractions in the uterus, the resulting recorded signals are unreliable because the electrodes record the summed electrical activity across multiple regions (e.g., contractile units) of the uterus. Consequently, it is difficult to tell which regions of the uterus generate the measured bioelectrical signals and thus it is difficult to determine if the different regions of the uterus are contracting in synchrony. Also, the signals recorded with the EKG pads are generally low with significant noise interference.

Figure 1A:
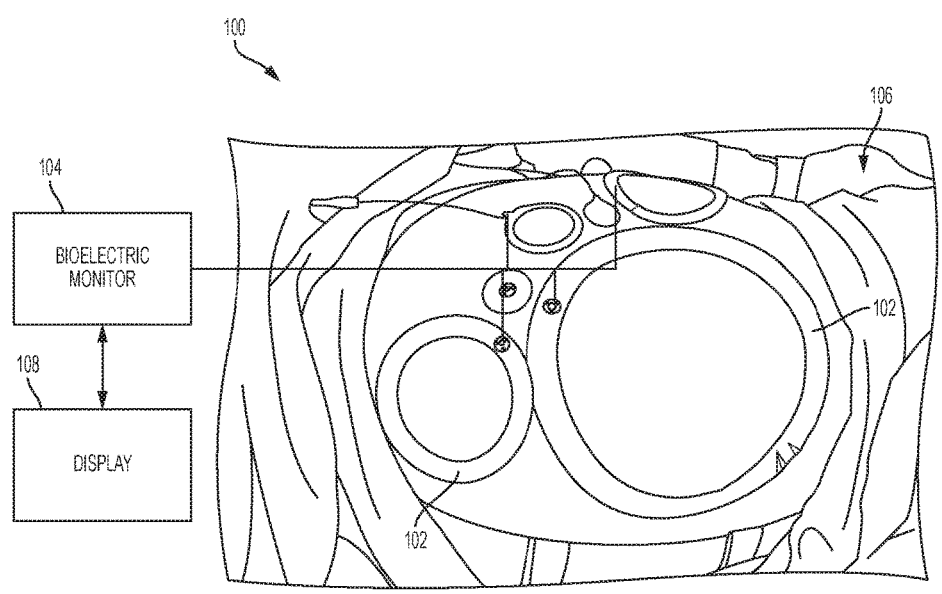
FIG. 1A illustrates an example system for measuring bioelectrical signals.

FIG. 1A illustrates an example system 100 for measuring bioelectrical signals. The system 100 includes a plurality of area electrodes 102. Each of the area electrodes 102 are coupled to a bioelectric monitor 104, and the bioelectric monitor 104 uses the area electrodes 102 as inputs to detect electrical signals generated by the patient 106. The signals detected by the bioelectric monitor 104 can be presented to a user via the display 108.

As illustrated, the system 100 can include a bioelectric monitor 104. The bioelectric monitor 104 can be a fetal monitor, electrocardiogram monitor, electromyogram monitor, or other type of patient monitor capable of detecting and/or recording electrical signals from a patient. The bioelectric monitor 104 can be configured to have between 1 and 32 (or more) inputs. The bioelectric monitor 104 can use a signal recorded at one or more of the inputs as a reference or ground signal, which can be subtracted or otherwise removed from the signals recorded at the other inputs of the bioelectric monitor 104. The bioelectric monitor 104 can include an amplifier to amplify the signals received at each of the inputs. The analog signals received from the area electrodes 102 at each of the inputs can be digitized with an analog to digital converter with an 8, 10, 12, 24, or 32-bit resolution. The digitized signals can have a sampling rate between about 128 Hz and about 1 kHz, between about 128 Hz and about 516 Hz, or between about 128 Hz and about 256 Hz. The bioelectric monitor 104 can include the display 108—for example, the bioelectric monitor 104 and the monitor 108 can be single unit. In other implementations, the display 108 can be a separate device, such as a monitor connected to a desktop computer.

In some implementations, the system 100 is configured to record bioelectric signals originating from the uterus, which can include uterine and fetal bioelectric signals. The uterus includes a plurality of contractile units. Each of the contractile units are about 8 cm×8 cm, and include muscle cells grouped into a syncytia. A syncytia is the smallest functional electrical unit in the uterus and is about 1 cm to about 2 cm wide. Each of the syncytia within a contractile unit are coupled together by gap junctions or connexins. Electrical activity does not propagate between separate contractile units of the uterus, but rather the organ-level contractions of the uterus occur through a mechanotransduction recruitment mechanism. Organ-level contractions (e.g., the contraction of substantially all of the contractile units) are indicative of true labor. In other implementations, the system 100 is configured to record additional bioelectric signals such as maternal cardiac signals.

The system 100 can include one or more area electrodes 102. The area electrodes 102 are described in further detail in relation to FIGS. 2-14. As an overview, the area electrodes 102 are ring electrodes that are configured to detect electrical signals originating from the uterus or other muscle-containing intra-abdominal organ. In some implementations, each of the electrodes 102 in the system 100 can be configured the same or differently. For example, each of the area electrodes 102 can have the same shape and size or a different shape and size. The electrodes designed for use in electroencephalogram (EEG) and EKG recordings (e.g., "pad" electrodes) are relatively poor at detecting signals originating from the uterus. The heart has a fixed pacemaker and fixed electrical conduction pathways that coordinate contractions. The largest electrical field vectors generated by the heart are substantially directed parallel with the skin of the patient. However, the uterus generates field vectors that run substantially perpendicular to the skin. The pad-type electrodes used in EEG and EKG recordings fail to detect the field vectors that run substantially perpendicular to the skin. The area electrodes 102 are configured to detect the perpendicular field vectors with a greater signal to noise ratio (SNR) when compared to pad-type electrodes. In some implementations, the area electrodes 102 can be used in combination with the pad electrodes.

More generally, the area electrodes 102 have an outer diameter (OD) and an inner diameter (ID) with the area there between defining an electrode body. The use of one or more area electrodes 102 placed on the abdomen of the patient can provide larger signals with improved spatial resolution. In order to increase spatial resolution and/or signal strength of bioelectrical signals originating in the uterus with greater accuracy and efficiency, one, two or more area electrodes can be arranged on the abdomen of the patient. In some implementations, the area electrodes 102 are configured to increase signal detection to bioelectric signals arising from a source perpendicular to the area electrode 102 when placed, and to substantially reject signals originating from sources parallel to the area electrode 102. For example, the area electrode 102 can reject about 90%, 80%, 70%, 60%, 50%, 40%, 30%, and 20% of signals originating from sources parallel to the area electrode 102. In some implementations, as also illustrated in reference to FIG. 14 below, the area electrode 102 can be configured to substantially reject other signals that are not of interest. The signals not of interest can include 60 Hz environmental noise, "shot" noise or other noise generated by the movement of the area electrode 102, and biological noise such as the electrical signals generated from muscles not of clinical interest at the time of the recording.

In some implementations, the shape of the area electrode 102 is configured to enable the area electrode 102 to substantially reject electrical signals of non-interest (e.g., noise and those generated substantially parallel to the surface of the skin) For example, electrically active tissue generates an oscillating dipole field. The dipole field is transmitted through the body, where it can be detected by an electrode. When the dipole comes into contact with the electrode, a chemical reaction occurs and releases (or absorbs) electrons and creates a voltage differential that is measured by the bioelectric monitor 104. For a solid, pad style electrode, a dipole field hitting the pad electrode from any direction can create a voltage differential that is measured by the bioelectric monitor 104. In comparison, the area electrode 102 can generate a different magnitude voltage differential responsive to the angle at which the dipole comes into contact with the area electrode 102.

In some implementations, the area electrode 102 includes a conductive gel layer. The gel layer can substantially cover the patient facing portion of a metal layer of the area electrode 102. The gel layer can include electrolytes and can improve electrical coupling between the metal of the area electrodes 102 and the patient's skin by reducing the resistance across the skin-metal barrier.

Figure 1B:
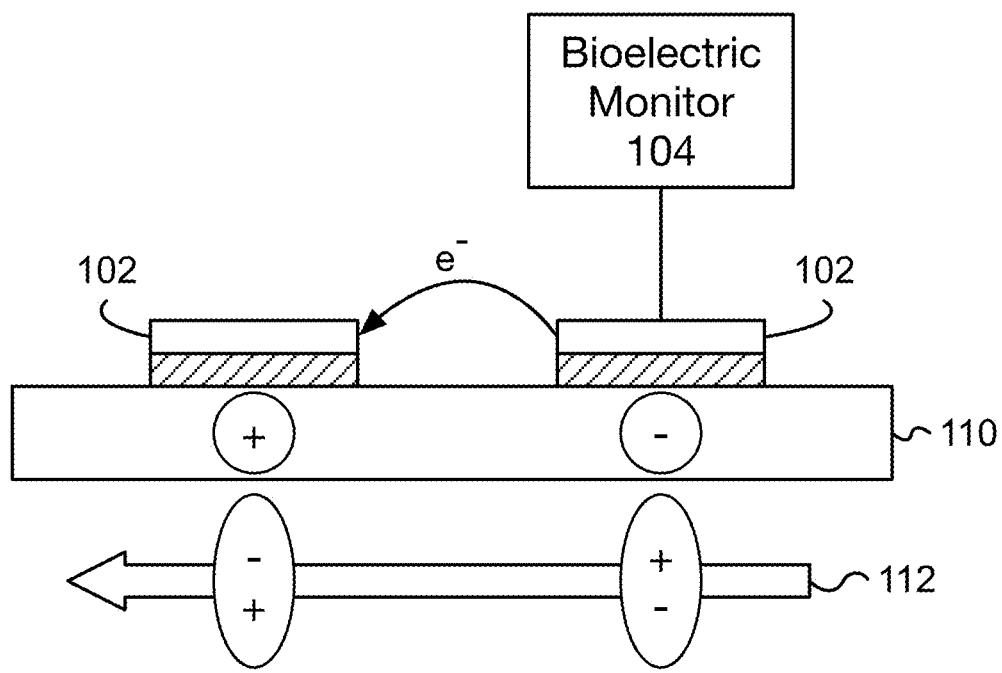
FIG. 1B illustrates a cross-sectional view of an example area electrode for use in the system illustrated in FIG. 1A as a dipole field travels parallel to the skin of a patient.

FIG. 1B illustrates a cross-sectional view of an example area electrode 102 as a dipole field travels parallel to the skin. FIG. 1B illustrates two portions of an area electrode 102, which are electrically coupled together via an out of plane portion of the area electrode 102. The area electrode 102 is coupled to the skin 110 as a dipole field 112 travels right to left and parallel to the patient's skin 110, as may occur with a dipole field generated by the maternal heart. The area electrode 102 is coupled to a bioelectric monitor 104. As the dipole field 112 travels right to left and comes into contact with the right portion of the area electrode 102, an electron is released. The electron travels to the left portion of the area electrode 102 where the generated voltage differential generates the reverse chemical reaction than that which occurred in the right portion of the area electrode 102. The electron generated at the right portion of the area electrode 102 is consumed in the chemical reaction occurring at the left portion of the area electrode 102. Because the electron released on the right portion of the area electrode 102 is consumed by the chemical reaction occurring on the left portion of the area electrode 102, the electron does not generate a voltage differential to be detected by the bioelectric monitor 104.

Figure 1C:
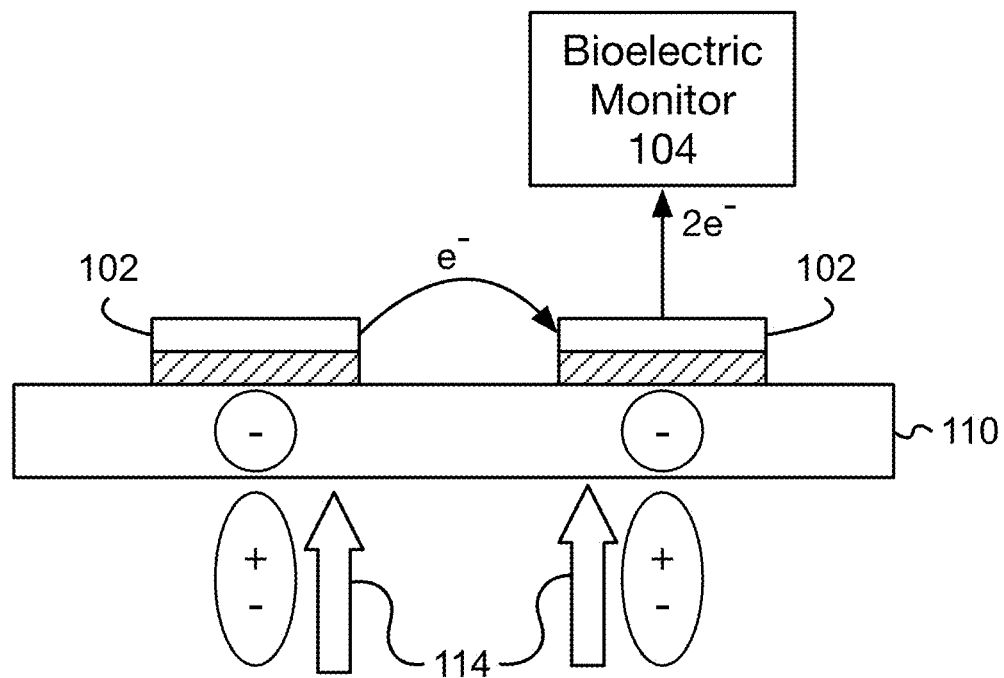
FIG. 1C illustrates a cross-sectional view of the example area electrode for use in the system illustrated in FIG. 1A as a dipole field travels perpendicular to the skin of a patient.

FIG. 1C illustrates a cross-sectional view of the example area electrode 102 as a dipole field 114 travels perpendicular to the skin. As illustrated in FIG. 1C, the dipole field 114 is traveling up from below the area electrode 102. For example, the dipole field may have originated in the uterus or a fetus. The dipole field 114 contacts both portions of the area electrode 102 substantially the same time, which synchronizes the chemical reactions and the release of electrons from both portions of the area electrode 102. The synchronized release of electrons enables the bioelectric monitor 104 to record voltage differential generated by the two electrons.

In some implementations, the system 100 includes a plurality of area electrodes 102. The system 100 can include between about 1 and about 8 area electrodes 102, between about 1 and about 6 area electrodes 102, or between about 1 and about 4 area electrodes 102. In some implementations, the area electrodes 102 can be used in combination with one or more standard pad electrodes. The use of a plurality of area electrodes 102 can enable the detection of the orientation and originating location of bioelectrical signals.

In some implementations, the area electrodes 102 can be placed in various arrangements on the abdomen of the patient. The area electrodes 102 can be arranged in an overlapping or non-overlapping manner. In an overlapping configuration, the area from which the area electrodes 102 detect signals can overlap without the area electrodes 102 physically overlapping. For example, a relatively smaller area electrode 102 may be placed within a relatively larger area electrode 102. When the area electrodes 102 are overlapping, the areas of the electrodes themselves may be slightly different, but the overlapping area electrodes can share, at least, a portion of the same region of, for example, the abdomen. In some implementations, the overlapping area of the area electrodes 102 can be concentric, so that the area electrodes 102 also share a same center point. In some implementations overlapping area electrodes 102 can increase spatial resolution. In some implementations, using non-overlapping area electrodes 102 can increase the signal strength recorded by the area electrodes 102. In some implementations, for obese patients, signal strength is generally reduced due to fat impeding bioelectric access to intra-abdominal organs. Accordingly, when measuring bioelectric signals from obese patients, the non-overlapping configurations may be used.

Figure 2B:
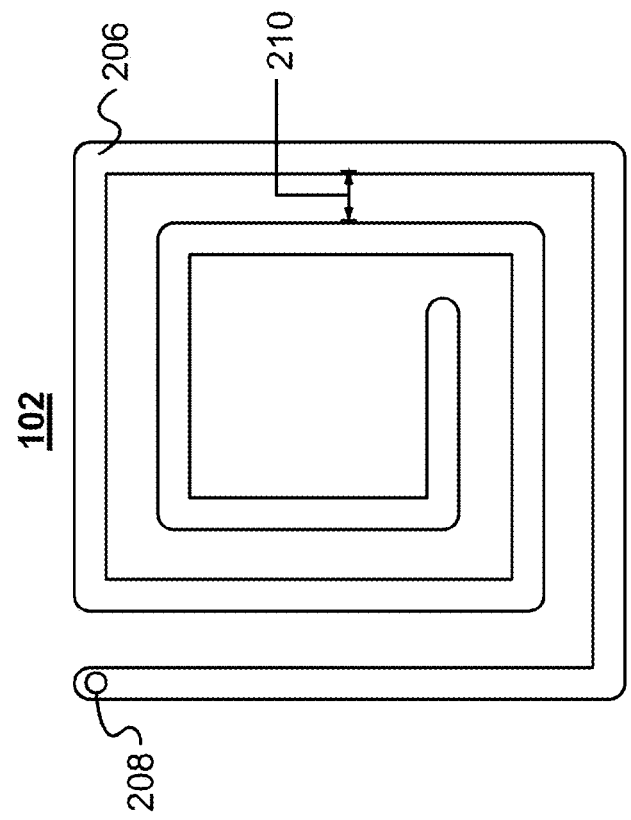
FIGS. 2A and 2B illustrate a schematic of a top view of example area electrodes for use in the system illustrate in FIG. 1A.
Figure 2A:
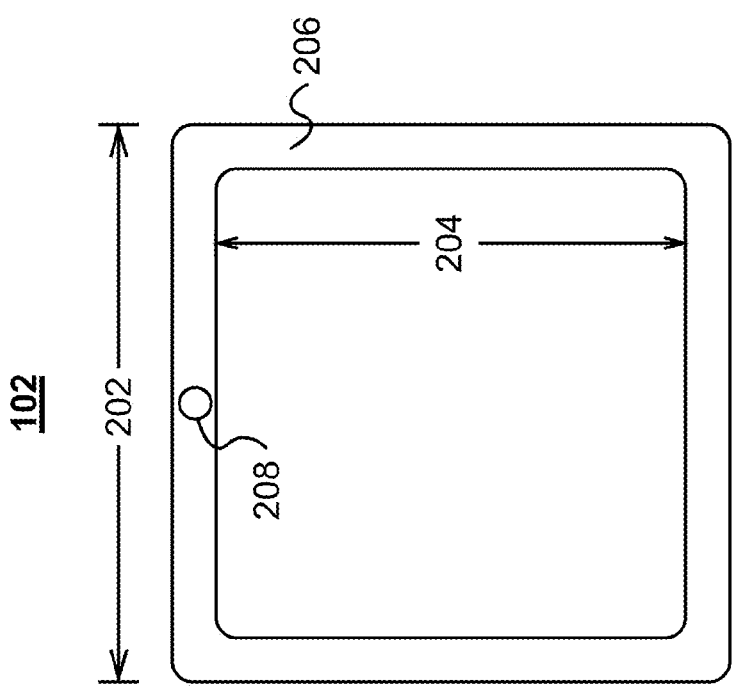

FIG. 2A illustrates a schematic of a top view of an example area electrode 102. The area electrode 102 has an outer diameter 202 and an inner diameter 204. The space between the inner diameter 204 and the outer diameter 202 defines the electrode body 206. The area electrode 102 also includes a connector 208.

As illustrated, the area electrode 102 is square shaped with rounded corners. In other implementations, the area electrode 102 is square shaped with blunt corners, rectangular shaped (with or without rounded corners), circular shaped, oval shaped, hexagonal shaped, or any other polygonal shape. The area electrode 102 illustrated in FIG. 2A forms a closed polygonal shape. In other implementations, the area electrode 102 can have an open configuration—for example, a circular shape with an open portion in the circular body of the area electrode 102. In some implementations, the outer diameter 202 is between about 3 cm and about 36 cm, between about 5 cm and about 25 cm, between about 5 cm and about 15 cm, or between about 5 cm and about 10 cm. The inner diameter can be between about 3 cm and about 30 cm, between about 4 cm and about 24 cm, between about 4 cm and about 14 cm, or between about 4 cm and about 9 cm. In some implementations, the width of the electrode body (e.g., the difference between the outer diameter 202 and the inner diameter 204) is between about 0.5 cm and about 5 cm, between about 0.5 cm and about 2.5 cm, between about 0.5 cm and about 1.5 cm, or about 0.5 cm and about 1.2 cm wide. In some implementations, the total area of the electrode body 206 is between about 5 cm$^2$ and about 900 cm$^2$, about 50 cm$^2$ and about 800 cm$^2$, about 100 cm$^2$ and about 600 cm$^2$, or about 200 cm$^2$ and about 400 cm$^2$. In some implementations, the electrode body 206 is formed from a metal layer. The metal layer can include silver-chloride, graphite, or other metal used for medical grade electrodes.

In some implementations, the size of the outer diameter 202, inner diameter 204, and electrode body 206 is configured responsive to the anatomical features generating the bioelectric signals. In some implementations, the size of the area electrode 102 is designed to be about the size of the largest contractile unit generating bioelectric signals. For example, when the area electrode 102 is configured to measure bioelectric signals from the uterus, which has a contractile unit of about 8 cm×8 cm, the outer diameter 202 of the area electrode 102 may be set to about 8 cm. In some implementations, at least one feature of the area electrode 102 is configured to be smaller than the tissue-level dipole oscillator. For the uterus, the tissue-level dipole oscillator is the syncytia, which is about 2 cm×2 cm. Accordingly, when the area electrode 102 is configured to measure bioelectric signals from the uterus the electrode body 206 has a width (e.g., the distance from the inner diameter 204 to the outer diameter 202) of about 1.5 cm.

In some implementations, the size and shape of the area electrode 102 enable the area electrode 102 to act like an antenna and resonate with the oscillating bioelectric signals. The frequency (f), propagation speed (c), and wavelength (λ) of the moving dipole field that generates the bioelectric signals are related by the wave equation, where λ=c/f. In some implementations, the bioelectric signal generated during uterus contractions has a frequency about 1 Hz. The rate of propagation of the bioelectric signal is about 3 cm/sec. Using the wave equation, the wavelength of the signal is about 3 cm. In some implementations, an antenna couples to a signal when one of the dimensions of the antenna is between ¼ and ½ of the signal wavelength. In this example, an antenna should have at least one dimension between about 0.75 cm and about 1.5 cm. Accordingly, in this example where the area electrode 102 is configured to detect contractions from a contractive unit of the uterus, the outer diameter of the area electrode 102 can be about 8 cm (corresponding to the size of a contractile unit) and the width of the electrode body can be about 1.5 cm (½ of the signal wavelength) to enable the area electrode 102 to couple to the bioelectrical signal generated by the contractive unit.

In some implementations, the size and shape of the area electrode 102 is selected responsive to the size, weight, and body mass index (BMI) of the patient. In some implementations, obese patients may require relatively larger area electrodes 102, such that an area electrode can be dimensioned specifically for a larger patient. For example, the area electrode 102 used for an obese patient may have a rounded square shape with outer sides measuring at 21 cm long and inner sides measuring at 18 cm long. In comparison, the area electrode 102 for a non-obese patient may have outer sides measuring about 9 cm and inner sides measuring about 6 cm.

In some implementations, obese patients require special consideration, depending on the degree of obesity. Because area electrodes detect signals from a direction pointed into the patient's abdomen and efficiently gather electrical signals, the number and sizes of the area electrodes used can be customized to optimize electrical signal detection from mildly obese (200 lbs. or a BMI between about 25 and about 30) to massively obese pregnant patients (more than 500 lbs. or a BMI above 30). In massively obese patients, the uterus is often a great distance from the abdominal surface, and electrical signals are attenuated by the intervening fat. At some degree of obesity, signal strength is anticipated to diminish and disperse such that increasing the size of the area electrode will be required to gather enough signal to determine the presence of a contraction. For massive obesity, the size of the electrode may need to be increased such that only very large area electrodes can detect electrical signal. This effect can reduce the optimal number of area electrodes, possibly to as low as one.

Still referring to FIG. 2A, the connector 208 of the area electrode 102 can be an electrical connector that enables the area electrode 102 to be coupled to an input of the bioelectric monitor 104. In some implementations, the connector 208 is a snap or button style connector, similar to those used in EKG electrodes. The snap connectors can replace traditional braided electrode connectors, although a combination of braids and snaps can be used. In some implementations, the snap connectors can be adapted for placement on the boundary of the area electrode, such that the size of the snap connectors can be smaller than the boundary or border width of the area electrodes.

FIG. 2B illustrates an example area electrode 102 configured in a spiral shape. The area electrode 102 has a width between about 3 cm and about 36 cm, between about 5 cm and about 25 cm, between about 5 cm and about 15 cm, or between about 5 cm and about 10 cm. In some implementations, the width of the electrode body (e.g., the difference between the outer diameter 202 and the inner diameter 204) is between about 0.5 cm and about 5 cm, between about 0.5 cm and about 2.5 cm, between about 0.5 cm and about 1.5 cm, or about 0.5 cm and about 1.2 cm wide. In some implementations, the total area of the electrode body 206 is between about 5 cm$^2$ and about 900 cm$^2$, about 50 cm$^2$ and about 800 cm$^2$, about 100 cm$^2$ and about 600 cm$^2$, or about 200 cm$^2$ and about 400 cm$^2$. In some implementations, the spacing 210 between each ring of the area electrode 102 is about ¼ of the wavelength (using the above wave equation) of the bioelectric signal to be detected.

In some implementations, the area electrode 102 can also include a plurality of separate electrode bodies. Each of the electrode bodies can be electrically coupled together by, for example, an electrical tether or wire. Each of the separate electrode bodies can be coupled to the patient and spaced apart from one another according to the above-described dimensions. For example, each of the electrode bodies can be a separate pad electrode or a strip electrode. The area electrode 102 may include four separate strip electrodes that are electrically coupled together. Each of the strip electrodes may be 1.5 cm wide and about 4 cm long. The four strip electrodes may be configured in a square shape (e.g., a first pair of the electrodes are placed parallel to one another and about 5 cm apart and a second pair of the electrodes are placed parallel to one another about 5 cm apart and perpendicular to the first pair of electrodes).

FIG. 3 illustrates an example electrode array 300. The electrode array 300 includes three area electrodes 102 coupled to an adhesive backing 302. In some implementations, the adhesive backing 302 holds each of the area electrodes 102 of the electrode array 300 in a predetermined spatial relationship (e.g., maintains a predetermined spacing between each of the area electrodes 102). In some implementations, the adhesive backing 302 is a repositionable backing that enables the electrode array 300 to be removed and repositioned on a patient.

In some implementations, as illustrated in FIG. 3, each of the electrodes have the same configuration. In other implementations, one or more of the area electrodes 102 can have a different electrode configuration. For example, one of the area electrodes 102 may have a larger inner and outer diameter than the other area electrodes 102, or one or more of the area electrodes 102 can have a different shape. For example, the array can include a larger area electrode 102 and then a smaller area electrode 102 positioned within the larger area electrode 102. In another example, one or more of the area electrodes 102 may be square shaped with rounded corners and one or more of the area electrodes 102 may be rectangular with rounded corners.

As illustrated in FIG. 3, the area electrodes 102 of the array 300 are arranged linearly. In other implementations, the area electrodes 102 are arranged in a nonlinear configuration. For example, the area electrodes 102 may be arranged inside of one another, in a triangular, cross, or circular configuration. The arrangement of the area electrodes 102 on the adhesive backing 302 can improve proper alignment of the area electrodes 102 on the patient. For example, the area electrodes 102 can be configured on the adhesive backing 302 to have a predetermined spacing between each of the area electrodes 102 such that when the electrode array 300 is placed, the proper spacing between neighboring area electrodes 102 is maintained. In some implementations, the electrode array 300 includes between 2 and 12 electrodes, between 2 and 10 electrodes, or between 4 and 6 electrodes.

Figure 4:
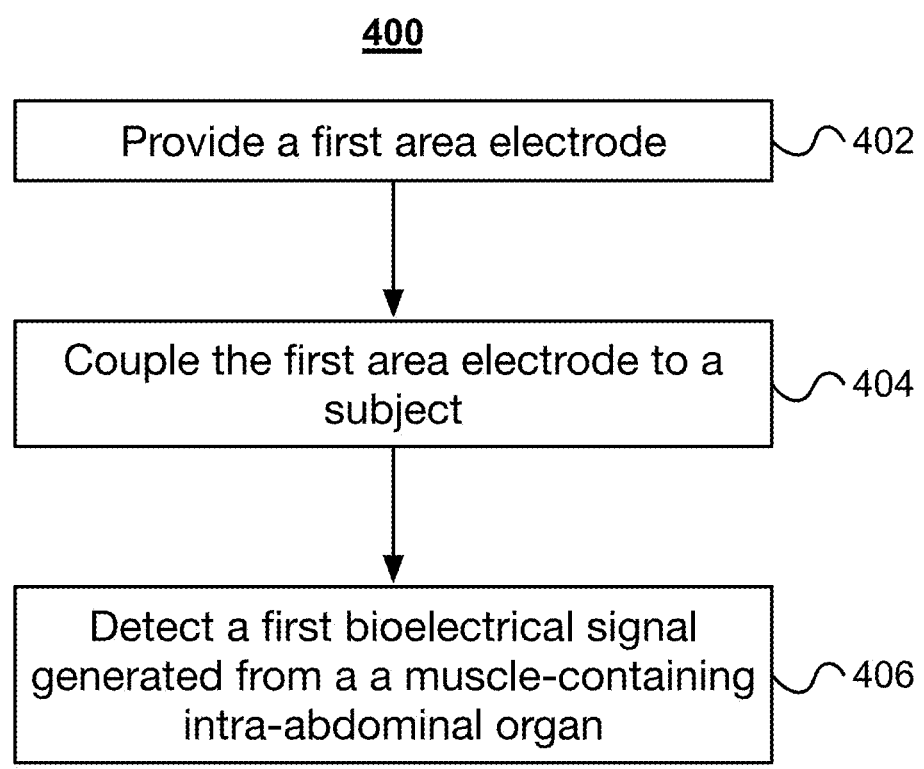
FIG. 4 illustrates a flow chart of an example method 400 for measuring bioelectrical signals using system illustrate in FIG. 1A.

FIG. 4 illustrates a flow chart of an example method 400 for measuring bioelectrical signals. The method 400 can include providing a first area electrode (step 402). The first area electrode is coupled to the abdomen of the patient (step 404). A first bioelectrical signal is detected with the first area electrode from a muscle-containing intra-abdominal organ in a patient (step 406).

As set forth above, the method 400 can include providing a first area electrode (step 402). The first area electrode can be any of the electrodes described herein. For example, the area electrode can be a ring (or other shaped) electrode that includes an electrode body defined in a metal layer by an inner and outer diameter. In some implementations, a plurality of area electrodes is provided. Each of the electrodes may be independent from one another or coupled together. For example, the electrodes may be configured in an electrode array where each of the area electrodes are coupled together by an adhesive layer. The area electrode can have one of a circular shape, a square with rounded corners shape, or a rectangle with rounded corners shape. In some implementations, the area electrodes are configured to detect electrical signals originating substantially perpendicular to a surface of the electrode body, and to substantially reject electrical signals originating substantially lateral to the surface of the electrode body.

Next, the first area electrode is coupled to the patient (step 404). The area electrode can be coupled to the abdomen of the patient. In some implementations, the patient is pregnant and the area electrode is used to detect bioelectrical signals originating from the uterus or a fetus within the uterus. In some implementations, the bioelectrical signals are recorded form the patient to determine if the patient is in labor or to monitor the fetus's heart rate. In some implementations, the area electrodes can include a tacky side that enables the first electrode to be reversibly coupled to the patient. In some implementations, one or more area electrodes can also be coupled to portions of the patient that are remote to the regions of interest (e.g., the uterus). The remotely placed area electrodes 102 can be used as a reference electrode, and can be, for example, coupled to the upper thigh of the patient.

Once the first area electrode is coupled to the patient, a bioelectric signal is recorded with the first area electrode (step 406). The first area electrode can detect bioelectrical signals generated substantially perpendicular to a face of the area electrode coupled to the patient while rejecting bioelectrical signals generated substantially parallel to the face of the area electrode coupled to the patient. In some implementations, the area electrode is configured to detect the bioelectric signals generated from a contractile unit within the uterus. Additional area electrodes may also be coupled to the patient's abdomen to detect bioelectric signals generated from other contractile units with the uterus. If a synchronization pattern is detected between the multiple area electrodes, for example the different area electrodes each detect bioelectric signals indicative of a contraction from the different contractile units, then the system coupled to the area electrodes may determine that the patient is in labor. The bioelectric signal can also be generated from a fetal or a maternal heart.

EXAMPLES

When observed, bipolar EMG recordings using standard pad electrodes have been shown to correlate with uterine contractions. Importantly, in many instances, contractions occur, even though pad-type EMG recordings are silent. In the data we report herein using area electrodes, all patients were in labor, experiencing regular uterine contractions, and the EMG recordings displayed in all figures correlate with a uterine contraction either as reported by the patient, or confirmed using clinical recording of uterine contractions, such as tocodynamometer "toco" recordings or intrauterine pressure catheter (IUPC) recordings. Toco recordings are made from a plunger device that records shape changes of the uterus when contractions occur, and do not rely on the bioelectrical properties of the uterus. For obese patients, toco recording is often unreliable since the shape changes of the uterus are physically distant from the plunger of the toco.

The following Examples have been included to provide guidance to one of ordinary skill in the art for practicing representative embodiments of the presently disclosed patient matter. In light of the present disclosure and the general level of skill in the art, those of skill can appreciate that the following Examples are intended to be exemplary only and that numerous changes, modifications, and alterations can be employed without departing from the scope of the presently disclosed patient matter.

Example 1

Comparison of Area Electrodes to Standard Bipolar Technique in Assessing Regional Contractions At least one area electrode can be placed onto the abdomen of a patient in order to assess contractions of intra-abdominal muscles. For example, two or more area electrodes can be used to provide a complete assessment of a plurality of contractions in the uterus of the patient. In some aspects, there can be two or more area electrodes or only one area electrode.

Figure 5:
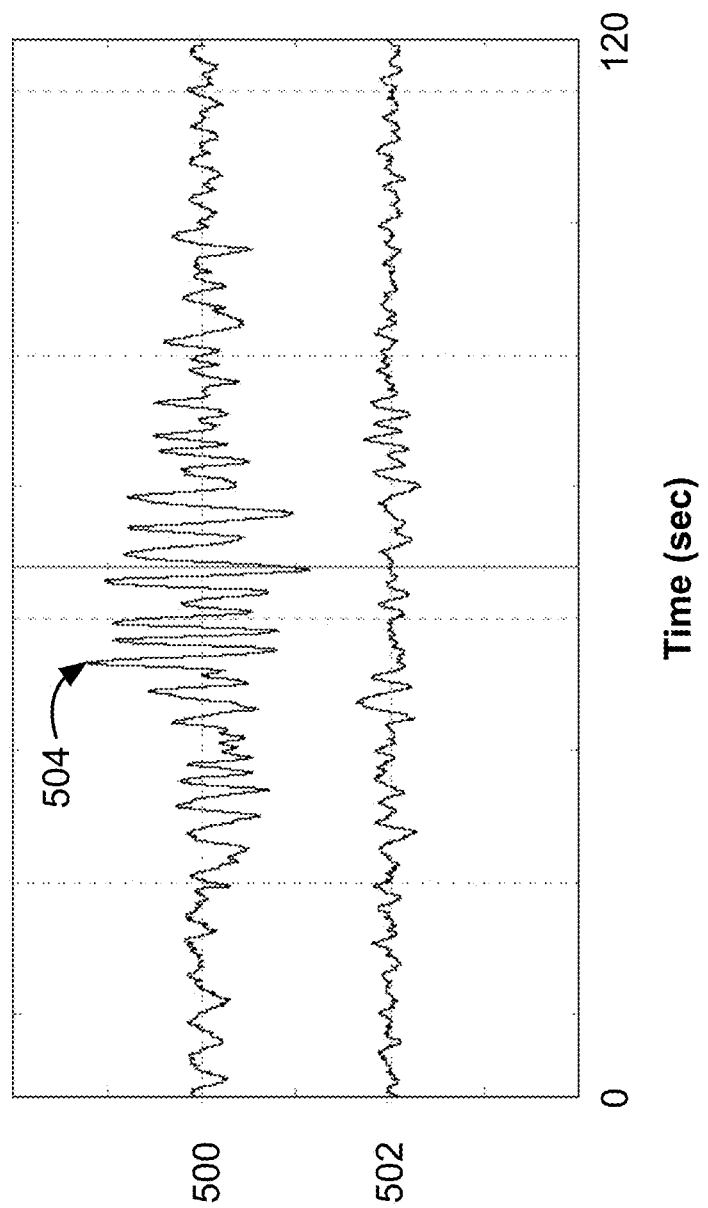
FIGS. 5-14 illustrate example recordings make with the area electrodes described herein.
Figure 6:
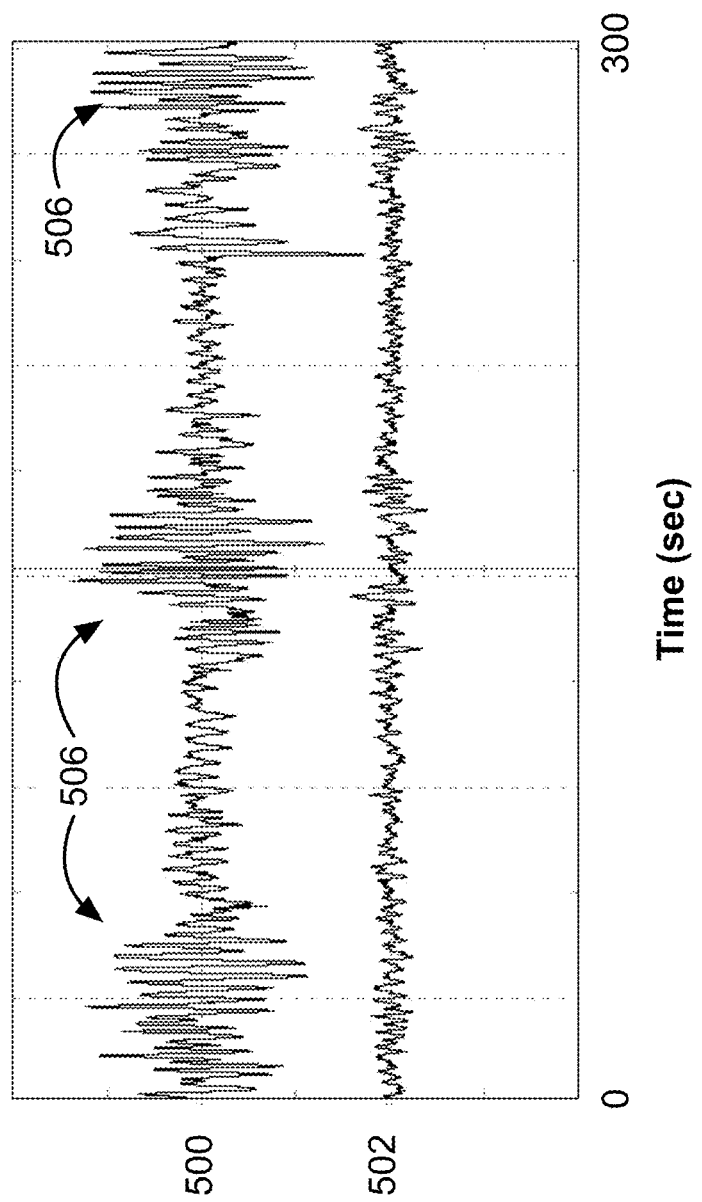

In FIGS. 5 and 6, for example, an electrode as described herein is used to assess regional contractions. Here, an area electrode can be a 12 cm (OD) ring electrode placed on the abdomen in order to assess regional contractions; although other sizes and shapes of the at least one area electrode are contemplated. Using ring electrodes can be beneficial in identifying regional contractions since the ring shape of the area electrode allows separating out different regions.

FIGS. 5 and 6 illustrate two traces of signals recorded from the abdomen of a patient in order to assess regional contractions in intra-abdominal muscles (e.g., the uterus) using a single area electrode of the present disclosure in comparison with a standard bipolar electrode pad technique, i.e., two electrode pads spaced apart. The trace 500 was collected using the above-described ring area electrode of the present disclosure. The area electrode is placed on the abdomen in order to assess regional contractions. The 502 trace was collected using a standard bipolar electrode pad technique.

As illustrated, the trace 502 recorded by the standard bipolar electrode pads is barely discernable due to substantial noise interference, while the trace 500 recorded by the electrode of the present disclosure is clearly discernable. Contractions reported by the patient and as seen on the clinical toco corresponded to the occurrences of the bioelectrical signals of the area electrodes. For example, specifically looking at the signal surrounding the 120 second mark (total time interval being between 3:07:00 and 3:08:00) in the trace 500, a bioelectrical burst 504 is apparent, which is indicative of a contraction of the intra-abdominal muscle. In contrast, the bioelectrical burst of the trace 502 was not visually apparent using standard bipolar electrode pads. FIG. 6 illustrates the same data illustrated in FIG. 5, but with a different time frame. In FIG. 6, it is apparent that three consecutive contractions 506 occurred during the longer time frame, which was detected in the trace 500, but not in the trace 502. In these examples and others, we observe the signal-to-noise ratio of the area electrodes is much superior to pad electrodes.

Figure 7:
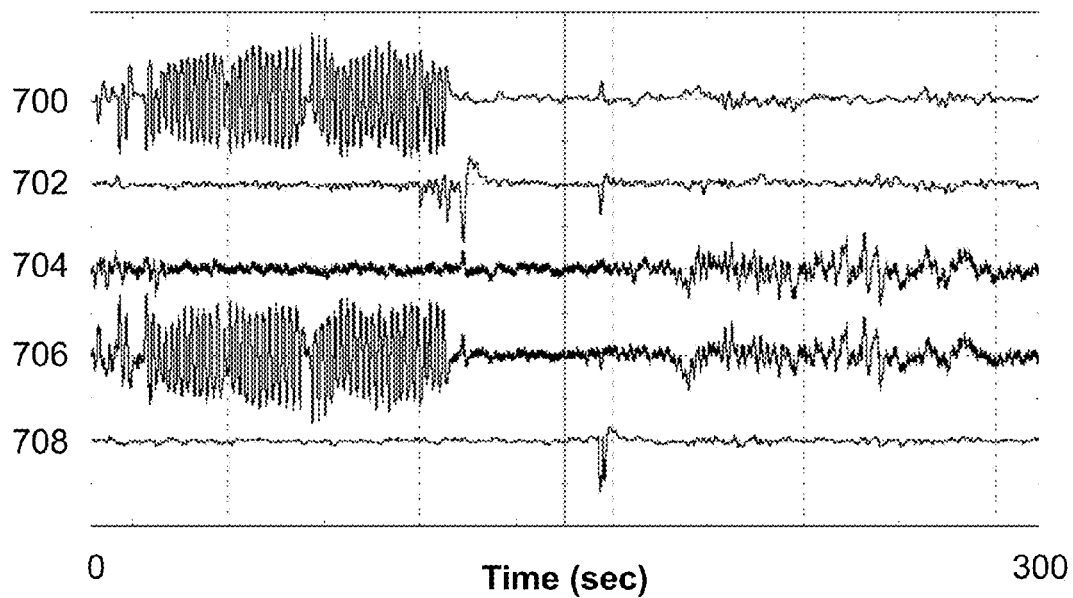
Figure 8:
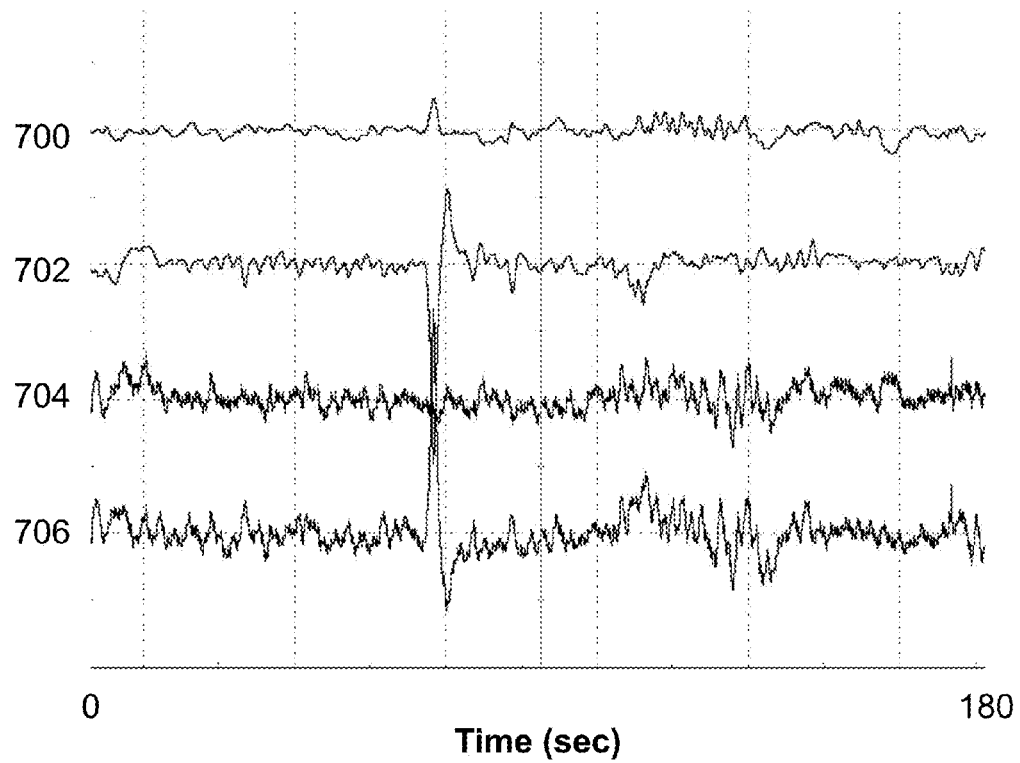

In comparison, FIGS. 7 and 8 illustrate traces generated using two electrodes of the present disclosure (e.g., first and second area electrodes). FIG. 8 illustrates a magnified portion of the traces illustrated in FIG. 7. The first and second area electrodes are placed on the abdomen in order to assess regional contractions. Each of the first and the second area electrodes are 12 cm (OD) ring electrodes as described above. A circle pad electrode is placed in a center of each of the first and the second area electrodes. The first and the second area electrodes can be referenced to one another and to the circle pad electrode placed in the center of the respective first and second electrodes. Referencing can be achieved by subtracting the voltages of one area electrodes from the other in order to determine the total separation of the bioelectrical signals in each of the area electrodes.

In some aspects, the recorded signals from either one or both of the first and second area electrodes and circle pads electrodes can be filtered to reduce the SNR. This can allow any bioelectrical bursts recorded to be more visually discernable. For example, a high pass and/or a low pass filter can be implemented.

In FIG. 7, the top trace 700 is illustrative of the first area electrode referenced to a circular pad electrode in a center of the abdominal ring. The second trace 702 is illustrative of the second area electrode referenced to a pad electrode in a center of the second area electrode. The third trace 704 is illustrative of a pad electrode placed in the center of the second area electrode referenced to a pad electrode placed in the center of the first area electrode. The fourth trace 706 is illustrative of the second area electrode referenced to the center of the first area electrode. The fifth trace 708 is a dual pad arrangement using a bipolar amplifier that is the most commonly used method of recording uterine EMG by others, and is displayed to allow comparison with our method. Each of the top four traces illustrate the voltage differences between electrode pairs of the area electrodes. Here we show that the area electrodes express a directional signaling dependent on the location of the reference electrode, and also dependent on whether the comparison electrode is an area electrode of the present disclosure or a pad.

To summarize the data, trace 700 illustrates a large signal with a specific fingerprint in the first third of the frame, with no signal later. Trace 702 shows only a brief signal occurring at the conclusion of the first third. Trace 704 shows a small voltage signal occurring at the last third of the frame (this signal is easily distinguished, but is not much more than the noise level). Trace 706 shows the same fingerprint signal at the same time as in trace 700, except inverted, plus the same smaller signal seen in trace 704. Trace 708, the bipolar signal, shows only a brief noise in the latter half of the tracing.

Analysis now shows that the large signal seen in trace 700 arises from the area below that first area electrode, as the comparison point is from within that area. This indicates that a contraction is occurring deep in the patient's abdomen, directly beneath the first area electrode. Trace 702 displays voltages arising only from the area beneath the second area electrode, since the comparison point is within this area—and the lack of signal indicates no contraction occurs directly beneath the second area electrode. Trace 704 mimics a pair of bipolar leads probing the signal that occurs on the skin between the area electrodes, and indeed the small signal is observed, but the large signal is completely missed. In trace 706 the second area electrode is referenced to the circle pad electrode remotely located within the first area electrode, and records both the deep and surface signals, but since the signals are referenced to a remote pad, the noise is higher. Thus the area electrode/remote pad combination records both surface and deep electrical signals, but the addition of the surface signals is obtained in a trade-off for increased noise.

Contrastingly, the signal recorded by standard bipolar electrode pads (e.g., trace 708) illustrates that the standard bipolar electrode pads, by themselves, were not able to accurately assess whether a true labor contraction occurred.

To summarize, these traces indicate that (1) area electrodes, as described herein, yield larger electrical signals with less noise, greatly improving SNR over conventional pad electrodes; (2) area electrodes as described herein observe uterine signals when standard pad electrodes do not, suggesting area electrodes probe in a direction pointed into the body, while standard pad probe electrodes measure bioelectrical signals directed parallel with the skin surface; (3) by directly comparing the signals recorded from different pairs of area electrodes, or area/pad pairs, it is possible to assign specific areas of muscle contraction activity within the abdominal cavity; and (4) area electrodes enable a determination to be made of whether a true labor contraction occurred. This directly indicates that area electrodes can delineate the location of the source of the electrical activity within the abdominal cavity, and demonstrates what we have termed spatial resolution, or directionality.

Example 2

Figure 9:
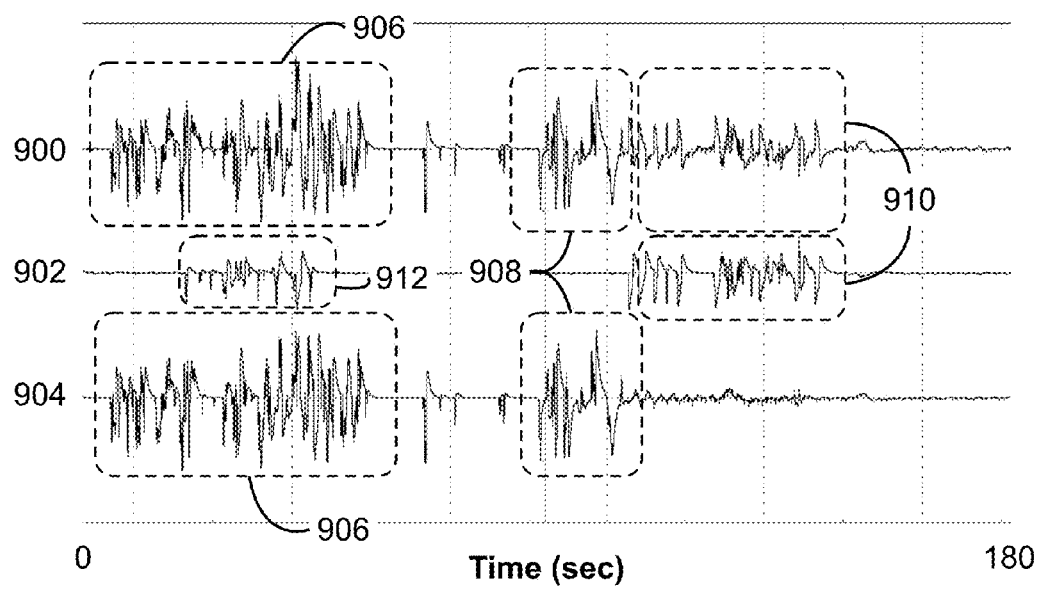
Figure 10:
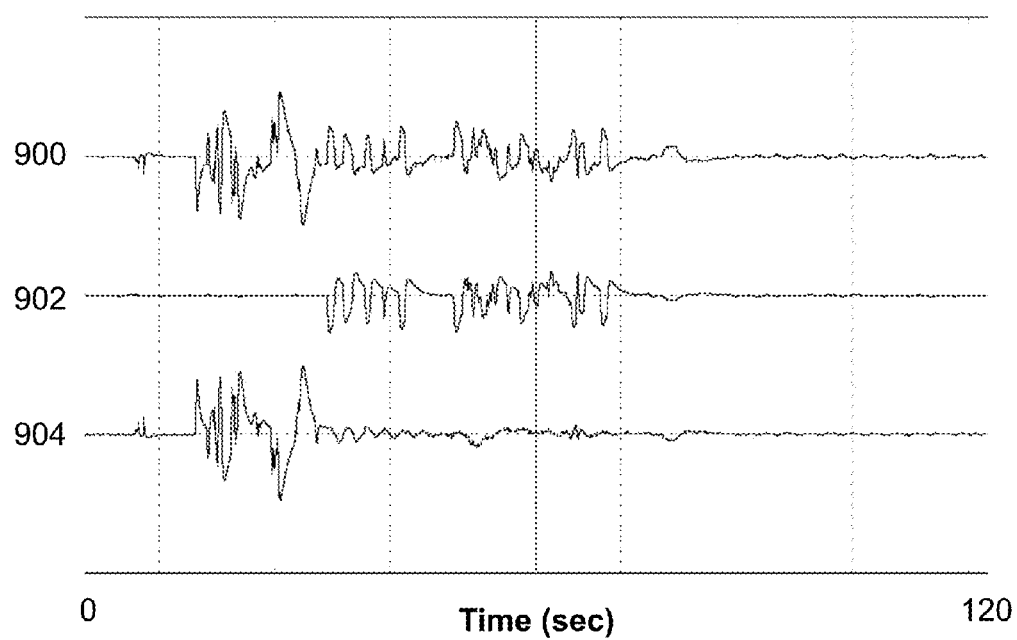
Figure 11:
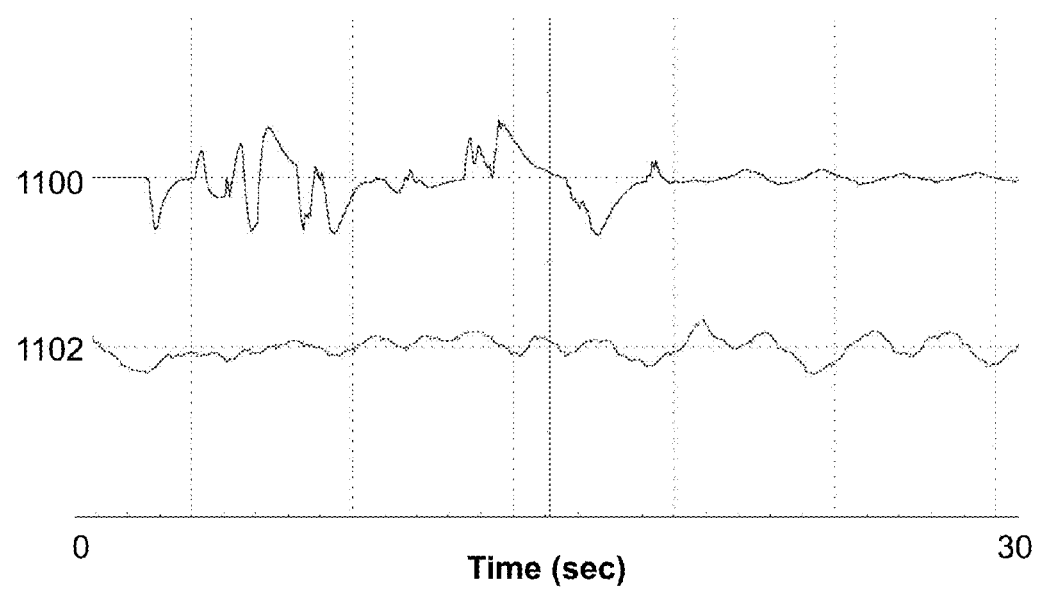

Comparison of Area Electrodes to Standard Bipolar Technique in Assessing Regional Contractions in Obese Patients The traces illustrated in FIGS. 9-11 differs from the data illustrated in FIG. 5 because the patient is considered clinically obese, with a body mass index (BMI) of 38 and above. In some aspects, obesity determination can be based on BMI, among other factors. In other aspects, obesity can be based on an abdominal girth measurement, among other factors. Regardless, with patients considered clinically obese, it is much harder to use standard bipolar electrode techniques to assess regional contractions in smooth muscles, like the uterus because the increased body fat impedes access to the smooth muscles. However, area electrodes have been found to record signals better than standard bipolar electrode techniques, as illustrated in Example 1.

In FIGS. 9-11, an analysis of area electrodes is used to assess regional contractions. Specifically, an analysis of area electrode as described herein is illustrated, where each area electrode is formed as a 12 cm (OD) circular ring. However, other shapes and/or sizes of the area electrodes can also be used in assessing regional contractions in obese patients (e.g., a 21 cm×21 cm rounded square).

The area electrodes were placed on the abdomen of the patient in order to measure bioelectrical bursts in the uterus, where arrangement of the area electrodes can vary. Three area electrodes were arranged in a triangle on the patient's abdomen, with each area electrode having a pad electrode positioned within the area electrode spanned by the area electrode. The area electrode can be numbered in any manner that can allow easy and comprehendible reference to each area electrode. For example, in the arrangement provided by FIGS. 9-11, the area electrodes can be arranged in a triangle and can be numbered 2, 4, 6, respectively, while the pad electrodes within each area electrode can be numbered 1, 3, 5, respectively.

In order to measure the bioelectrical bursts, each of the area electrodes was referenced to one another in order to reflect the voltages in each area electrode. For example, in FIG. 9, the top trace 900 is area electrode 2 minus area electrode 4; the middle trace 902 is area electrode 4 minus area electrode 6; the bottom trace 904 is area electrode 2 minus area electrode 6. As illustrated, the traces are large, approaching 400 µV.

It is seen that there are four time intervals showing electrical activity. The first interval is interval 906 (60 sec total duration) and appears in the trace 900 and 904. The second time interval 908 (10 sec total duration) appears in the trace 900 and 904. The third interval 910 (25 sec total duration) occurs in the traces 900 and 902. Lastly there is a fourth, smaller interval 912 (25 sec total duration), seen best in the middle trace 902.

Remembering that the traces 900, 902, and 904 represent signals from pairs of area electrodes, it is straight forward to assign each signal to a specific area electrode. Beginning with the inverted third interval 910, this is seen in the trace 900 and 902 but not in the trace 904. Thus this signal is from area electrode 4. The inversion reflects 4 being subtracted in one tracing, but not the other.

Next, consider the first interval 906, which is seen in trace 900 and trace 904, without inversion. Hence this signal arises from area electrode 2. Similarly, the second interval 908 is seen in the traces 900 and 904 without inversion and also can be assigned to area electrode 2. Finally, the fourth interval 912 is seen best in the trace 902, indicating the source is either 4 or 6, but the top and bottom tracings partially obscure visually seeing this smaller signal. Detailed analysis reveals, however, that the signal is present inverted in the trace 900, indicating the origin is area electrode 4.

We can therefore conclude that regional contractions beneath each area electrode occur over those time intervals. Furthermore, area electrode 4 demonstrates a regional contraction that occurs at the same time as another regional contraction (e.g., the fourth time interval 912 is simultaneous with the first time interval 906 of area electrode 2) and following another regional contraction (e.g., third time interval 910 follows the second time interval 908 of area electrode 2).

This demonstrates that regional contractions of the uterus can be detected using only area electrodes, and synchronous and asynchronous contractions of specific regions can be detected.

FIG. 10 illustrates an expansion of the time frame near the end of FIG. 9 to allow assessment of the small signals in the trace 904 that occurred after the second time interval 908. The trace 904 has been inverted in FIG. 10 subtracting 6–2 rather than 2–6 as was done in FIG. 9. It was not obvious in FIG. 9 if this small signal was unique, or part of the third interval 910 seen clearly in the tracing 902. Because of this expansion, the phase of oscillations (fingerprint) can now be seen to be unique, indicating the signal is not arising specifically beneath a single area electrode. This indicates that area electrodes 2 and 6 are functioning similarly to pad electrodes, and display a signal that originated along the skin between the area electrodes. To emphasize the scale of the tracings, these "small signals" are still 50 µV, and quite sufficient to define contractile activity. Thus, area electrodes separated by some distance retain all the advantages of area electrodes with regard to gathering large signals and reporting directionality, but furthermore can report surface signals similarly to pad electrodes. This dual functioning can assist with determining if the bioelectrical signal arising from the entire uterus is captured by a specific physical arrangement of the area electrodes (in this example it is not between area electrode 2 and 6). Thus, the presence or absence of surface signals will assist with defining the fidelity of capturing all electrical signals originating from the entire intra-abdominal cavity.

In comparison with both FIGS. 9 and 10, FIG. 11 illustrates the same data expanded only about area electrode 2 referenced to area electrode 6. The first trace 1100 illustrates area electrode 2 minus area electrode 6. The second trace 1102 illustrates the pad electrode 1 in the center of area electrode 2 referenced to the pad electrode 5 in the center of the area electrode 6 (electrode 1-electrode 5). From this data, the pad electrodes reveal a barely visible maternal heart rate signal, but no clear uterine bioelectrical signal. A high pass filter of 0.4 Hz and a low pass filter of 0.8 Hz were used to filter the traces illustrated in FIG. 11. Using the pads in the centers of the area electrode ensured that the pads spanned an area with known contractile activity. These data indicate that the standard pad electrodes, in some cases, do not display signals, despite the proven occurrence of contractions underneath the electrodes. This lends further support to our other observations that area electrodes record signals that originate from within the patient's abdomen, and the pad electrodes record voltage differences across the surface of the skin.

Example 3

Figure 12:
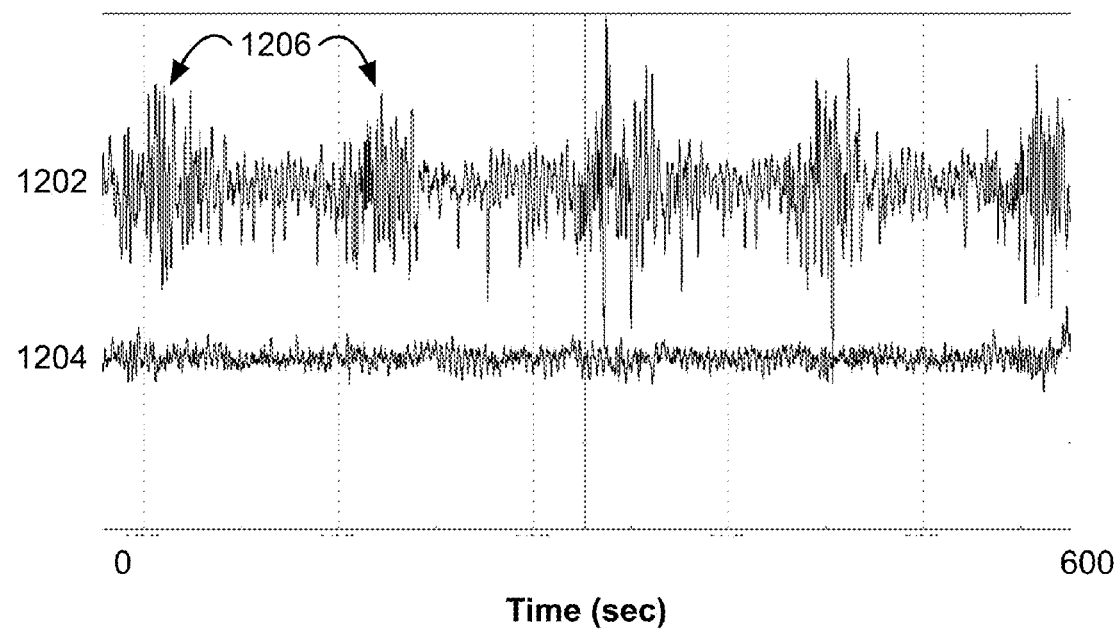
Figure 13:
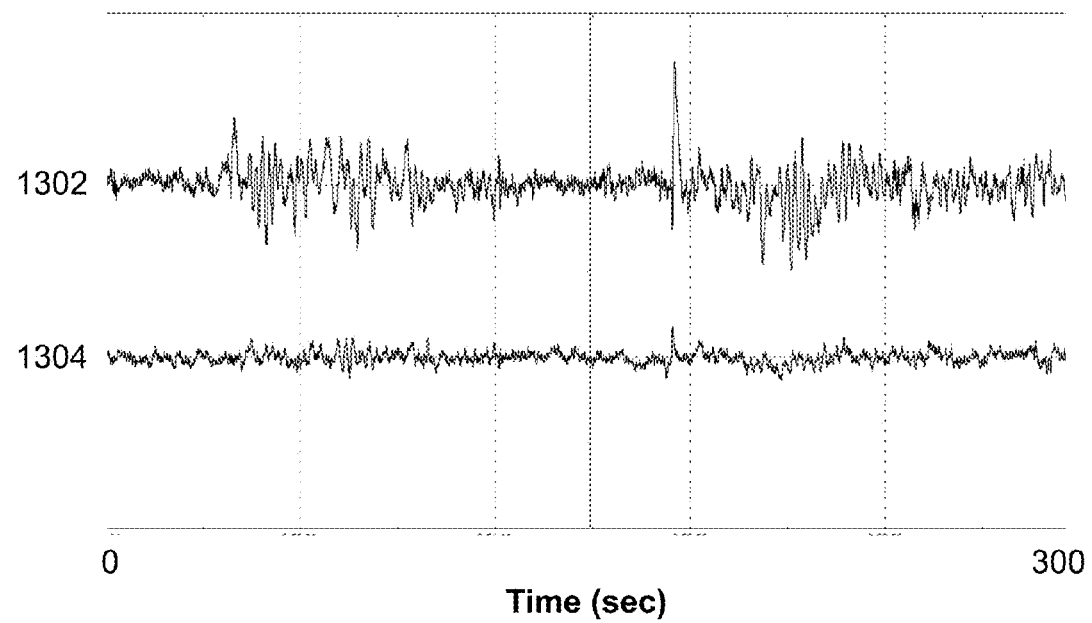

Comparison of Area Electrodes to Standard Bipolar Technique in Assessing Active Labor FIGS. 12 and 13 illustrative traces of a patient in active labor. To measure active labor, at least one area electrode can be placed onto a patient's abdomen in order to non-invasively assess regional contractions of the uterus.

In FIGS. 12 and 13, an area electrode is compared against other conventional techniques, such as the standard bipolar technique. The standard bipolar technique included placing two pad electrodes 5 cm apart on a patient's abdomen. An amplifier can amplify the signal(s) recorded by the electrodes in order to simultaneously display the signal voltage over time for the at least one area electrode and/or the standard bipolar pad electrodes.

FIGS. 12 and 13 illustrate assessing contractions in order to ascertain whether the patient is experiencing labor contractions. In both FIGS. 12 and 13 the top trace 1202 is the signal recorded by the area electrode, while the second trace 1204 is the signal recorded by standard bipolar electrode pads. Accordingly, the signal recorded by the standard bipolar electrode pads is barely discernable due to substantial noise interference, while the recorded signal recorded by the area electrode is clearly discernable. Specifically, in FIG. 12, the trace 1202 shows five bioelectrical bursts 1206 of about 60 second duration, each separated by about 60 to about 90 seconds, which are indicative of five consecutive uterine contractions. However, the five bioelectrical bursts were not picked up by the standard bipolar electrode pads, as can be seen in the trace 1204. These traces further demonstrate the superior signal gathering capabilities of the area electrode over the bipolar pad arrangement, but primarily serve to demonstrate that area electrode can record as many as 5 contractions over 10 minutes. Determining whether the contractions are indicative of true or active labor can be accomplished by using at least 2 and up to 20 area electrodes, thereby determining the presence or absence of synchronization of the area electrode signals. We conclude that the presence of absence of true labor can be determined using only 10 minutes of monitoring the patient.

True or active labor can be defined by a synchronization of regional contractions in the uterus (e.g., the regions are in a state of contraction during the same time period). In some aspects, there can be 20 regions (as defined by a contractile unit) of the uterus. For a patient to be in true labor, substantially all 20 regions must contract in synchrony. In other implementations, between 2 and 20, between 5 and 20, between 10 and 20, or between 15 and 20 of the regions contract in synchrony. In order to measure the synchronized contraction of these regions, at least one area electrode can be placed onto the patient's abdomen. In some aspects, the area electrode can be a 5 cm ring electrode. As discussed above, other sizes and shapes can also be contemplated.

In some aspects, the recorded signal from either one or both of the at least one area electrode and the standard bipolar pad electrodes can be filtered to reduce the SNR. This will allow any bioelectrical bursts recorded to be more visually discernable. For example, a high pass and/or a low pass filter can be implemented, where such filters may be optimal for standard bipolar techniques. A 0.3 Hz high pass and a 0.8 Hz low pass filter can be used.

The data illustrated in FIG. 13 differs from that in FIG. 12 because the patient is considered very obese, with a BMI of 42 (in comparison, the patient in FIG. 12 has a BMI of 32). With patients considered clinically obese, it is much harder to use the standard bipolar electrode technique to determine whether the patient is having a contraction. This is because the increased body fat impedes access to the uterus. However, area electrodes have been found to pick up signals better than standard bipolar electrode techniques, even in very obese patients. This is apparent in the trace 1302 of FIG. 13, where the signal recorded by the at least one area electrode has a diminished absolute voltage value in comparison to the signal recorded by the at least one area electrode in the first trace 1202 of FIG. 12. Yet, the SNR remains similar to that in FIG. 12 and the bioelectrical bursts indicative of contractions are still easily discernable. Contrastingly, the signal recorded by the standard bipolar electrode pads can perhaps be visually observed in the trace 1304 of FIG. 13, but would require detailed signal processing in order to determine the presence of a contraction. Therefore, the standard bipolar electrode pads, by themselves, are not able to accurately assess whether a very obese patient is contracting, or in true labor, while area electrodes are capable of determining if a very obese patient is having a labor contraction.

Example 4

Figure 14:
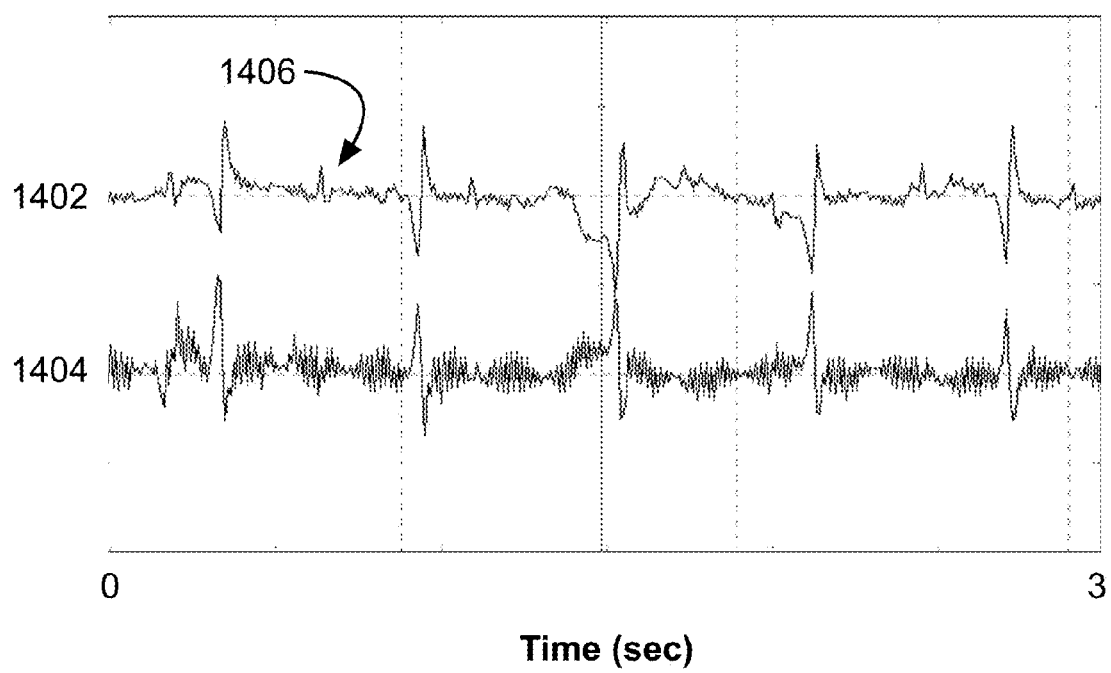

Comparison of Area Electrodes to Standard Bipolar Technique in Assessing Fetal Heart Rate FIG. 14 illustrates detecting a fetal heart rate with the electrodes of the present disclosure. An area electrode was placed onto a patient's abdomen. An area electrode can be place over the fetal thorax, which is within the maternal abdomen, in order to measure fetal and/or maternal heart rate. The area electrode was a ring electrode, although other shaped area electrodes can be used.

In FIG. 14, a trace made with the area electrode is compared against other conventional techniques, such as the standard bipolar technique. The standard bipolar technique included placing two pad electrodes 5 cm apart on the patient's abdomen.

In some aspects, the recorded signal from either one or both of the area electrode and the standard bipolar technique can be filtered to optimize bioelectrical signals from the heart or EKG, and omit uterine bioelectrical activity. An amplifier can amplify the signal(s) recorded by the electrodes in order to simultaneously display the signal voltage over time for the at least one area electrode and/or the standard bipolar pad electrodes.

In FIG. 14, the first trace 1402 is the signal recorded by the area electrode, while the second trace 1404 is the signal recorded by the standard bipolar electrode pads. For example, in FIG. 14, an EKG can be used to record the electrical activity of both the maternal and/or the fetal heart rate, where a 5 Hz high pass and a 100 Hz low pass filter can be used. Note that this filter window (5 to 100 Hz) excludes uterine bioelectrical activity, which occurs between 0.2 and 2 Hz. Also note the very low values on the scale of the voltage axis indicate very low signal sizes. The maternal heart rate is the obvious sawtooth signal, but the small fetal heart rate 1406 is also easily seen midway between the first two maternal EKG signals, then recurring periodically at 400 millisecond intervals. Accordingly, the signal recorded by the standard bipolar electrode pads in the second trace 1404 is barely discernable due to substantial noise interference. In particular, the EKG recorded by the standard bipolar electrode pads is obscured by noise at 60 Hz. Note that to record the EKG signals, 60 Hz is passed through the filter window (5 to 100) and hence is obscuring. Since area electrodes are directional, 60 Hz noise pickup is also directional and there is a concomitant reduction of noise with area electrodes relative to pad electrodes. By measuring the time between occurrences of the fetal heart beats, the fetal heart rate, in terms of beats per minute, can be immediately and successively calculated and recorded. In this case, 400 milliseconds between heart beats corresponds to a fetal heart rate of 150 beats per minute.

It will be understood that various details of the presently disclosed patient matter may be changed without departing from the scope of the presently disclosed patient matter. Furthermore, the foregoing description is for the purpose of illustration only, and not for the purpose of limitation.

CONCLUSION

While the following terms are believed to be well understood by one of ordinary skill in the art, the following definitions are set forth to facilitate explanation of the presently disclosed patient matter.

Following long-standing patent law convention, the terms "a", "an", and "the" refer to "one or more" when used in this application, including the claims.

Unless otherwise indicated, all numbers expressing measurements, conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed patient matter.

As used herein, the term "about", when referring to a value or to an amount of a length, width, mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including", "containing", or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed patient matter.

With respect to the terms "comprising", "consisting of", and "consisting essentially of", where one of these three terms is used herein, the presently disclosed and claimed patient matter can include the use of either of the other two terms.

As used herein, the term "and/or", when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

What is claimed:

1. A method for measuring at least one bioelectrical signal, the method comprising:
   providing a first area electrode comprising:
      a planar metal layer defining an electrode body having an inner diameter and an outer diameter, the inner diameter defining an opening in the planar metal layer, wherein the electrode body has a surface area between 5 $cm^2$ and 900 $cm^2$ and a width between 0.5 cm and 5 cm; and
      a connector in electrical communication with the metal layer;
   coupling the first electrode to an abdomen of a patient; and
   detecting a first bioelectrical signal with the first area electrode generated from a muscle-containing intra-abdominal organ in a patient.

2. The method of claim 1, wherein the muscle-containing intra-abdominal organ is a uterus.

3. The method of claim 1, further comprising detecting with the first area electrode an electrical signal generated by at least one of a fetal heart and a maternal heart.

4. The method of claim 1, further comprising:
   detecting, with a second area electrode, a second bioelectrical signal generated from the muscle-containing intra-abdominal organ in the patient, wherein the first bioelectrical signal is generated by a first contractile unit of the intra-abdominal organ and the second bioelectrical signal is generated by a second contractile unit of the intra-abdominal organ;
   detecting a synchronization pattern of the first and the second bioelectrical signals; and
   determining a labor status responsive to the synchronization pattern.

5. The method of claim 1, wherein the electrode body has one of a circular shape, a square with rounded corners shape, a hexagonal shape, or a rectangle with rounded corners shape.

6. The method of claim 1, wherein the first area electrode is configured to detect electrical signals originating substantially perpendicular to a surface of the electrode body, and to substantially reject a noise signal.

7. The method of claim 6, wherein the noise signal comprises at least one of electrical signals originating substantially lateral to the surface of the electrode body and environmental electrical noise.

8. The method of claim 1, further comprising determining a direction of an origination of the first bioelectrical signal.

9. The method of claim 1, further comprising referencing the first bioelectrical signal with a second bioelectrical signal from an electrode placed remote to the opening in the planar metal layer.

10. An electrode system comprising:
    a first area electrode comprising:
    a planar metal layer defining an electrode body having an inner diameter and an outer diameter, the inner diameter defining an opening in the planar metal layer, wherein the electrode body has a surface area between 5 $cm^2$ and 900 $cm^2$ and a width between 0.5 cm and 5 cm; and a connector in electrical communication with the metal layer.

11. The electrode system of claim 10, wherein the electrode body has one of a circular shape, a square with rounded corners shape, a hexagonal shape, or a rectangle with rounded corners shape.

12. The electrode system of claim 10, wherein the first area electrode is configured to detect electrical signals originating substantially perpendicular to a surface of the electrode body and to substantially reject a noise signal.

13. The electrode system of claim 12, wherein the noise signal comprises at least one of an electrical signal originating substantially lateral to the surface of the electrode body and an environmental electrical noise signal.

14. The electrode system of claim 10, further comprising:
a second area electrode;
a third area electrode; and
an adhesive layer, wherein the first area electrode is coupled to a first portion of the adhesive layer, the second area electrode is coupled to a second portion of the adhesive layer, and the third area electrode is coupled to a third portion of the adhesive layer.

15. The electrode system of claim 14, wherein the first, second, and third area electrode are configured in a row.

16. The electrode system of claim 14, wherein the first, second, and third area electrode are configured in a triangle.

17. The electrode system of claim 10, further comprising a second area electrode is positioned within the opening in the first area electrode defined by the inner diameter of the first area electrode.

18. The electrode system of claim 10, wherein the metal layer comprises silver-chloride.

* * * * *